(12) United States Patent
Fourmaux et al.

(10) Patent No.: US 11,438,997 B2
(45) Date of Patent: Sep. 6, 2022

(54) METHOD AND SYSTEM OF LASER-DRIVEN INTENSE X-RAY PHOTONS IMAGING

(71) Applicants: INSTITUT NATIONAL DE LA RECHERCHE SCIENTIFIQUE, Québec (CA); UNIVERSITY OF SASKATCHEWAN, Saskatoon (CA)

(72) Inventors: Sylvain Fourmaux, Drummondville (CA); Jean-Claude Kieffer, Montréal (CA); Emil Hallin, Riversides Estates (CA)

(73) Assignees: INSTITUT NATIONAL DE LA RECHERCHE SCIENTIFIQUE; UNIVERSITY OF SASKATCHEWAN

( * ) Notice: Subject to any disclaimer, the term of this patent is extended or adjusted under 35 U.S.C. 154(b) by 25 days.

(21) Appl. No.: 17/250,302

(22) PCT Filed: Jul. 4, 2019

(86) PCT No.: PCT/CA2019/050924
§ 371 (c)(1),
(2) Date: Dec. 30, 2020

(87) PCT Pub. No.: WO2020/006638
PCT Pub. Date: Jan. 9, 2020

(65) Prior Publication Data
US 2021/0219410 A1      Jul. 15, 2021

Related U.S. Application Data

(60) Provisional application No. 62/694,495, filed on Jul. 6, 2018, provisional application No. 62/823,059, filed on Mar. 25, 2019.

(51) Int. Cl.
*H05G 2/00* (2006.01)
*G01N 33/00* (2006.01)
*G01N 23/041* (2018.01)

(52) U.S. Cl.
CPC .......... *H05G 2/008* (2013.01); *G01N 23/041* (2018.02); *G01N 33/0098* (2013.01)

(58) Field of Classification Search
CPC ...... H05G 2/008; H05G 2/003; G01N 23/041; G01N 33/0098
See application file for complete search history.

(56) References Cited

U.S. PATENT DOCUMENTS

| 7,321,604 B2 | 1/2008 | Umstadter et al. |
| 8,705,692 B2 | 4/2014 | Umstadter et al. |

(Continued)

FOREIGN PATENT DOCUMENTS

| CA | PCT/CA2019/050924 A1 | 9/2020 |
| WO | WO 2015/087007 A1 | 6/2015 |
| WO | WO 2017/044484 A1 | 3/2017 |

OTHER PUBLICATIONS

Stefan et al. "A Plasma wiggler beamline for 100TW to PW lasers", High Energy Density Physics 8, Elsevier B.V., 2011, p. 133-140 (Year: 2011).*

(Continued)

*Primary Examiner* — David P Porta
*Assistant Examiner* — Mamadou Faye
(74) *Attorney, Agent, or Firm* — Lavery, De Billy, LLP; Gwendoline Bruneau

(57) ABSTRACT

A X-ray source, comprising a laser, of a pulse duration of at most 40 fs, instantaneous power of at least about 80 TW, a pulse repetition rate of at least 1 Hz; an optical compressor spectrally shaping the laser beam; focusing optics in the range between f#10 and f#15; and a gas target of electron (Continued)

density after ionization by the laser beam in a range between $10^{18}$ cm$^3$ and $10^{19}$ cm$^{-3}$; wherein the focusing optics focuses the laser beam in the gas target, and interaction of the focused laser beam with the gas target generates an X-ray beam, with a focused laser amplitude $a_0$, given by $a_0=0.855$ $[I_L (10^{18} W/cm^2)\lambda_L^2 (\mu m)]^{1/2}$, where $I_L$ is the on-target laser intensity and $\lambda_L$ is the laser wavelength, of at least 2 and a $P/P_c$ ratio value of at least 20, with P being the beam power and Pc a critical power given by Pc=17 ($n_c/n$) GW where n is the electron density and $n_c$ is a critical electron density at which the plasma acts as a mirror reflecting the laser beam.

18 Claims, 13 Drawing Sheets

(56) References Cited

U.S. PATENT DOCUMENTS

| | | |
|---|---|---|
| 9,678,405 B2 | 6/2017 | Mironov et al. |
| 2015/0324975 A1 | 11/2015 | Cope et al. |
| 2019/0115711 A1* | 4/2019 | Payeur .............. H01S 3/10061 |

OTHER PUBLICATIONS

Leonida et al. "Laser-Plasma Acceleration with FLAME and ILIL Ultaintense Lasers", www.mdpi.com/journal/applsci, Appl. Sci. 2013, p. 559-580. (Year: 2013).*

European Search Report issued in corresponding European patent application No. 19829893.7 dated Feb. 25, 2022.

Fourmaux et al., Radiation generation via non-linear optical processes during propagation of high peak and high average power fs pulses, Proc. of SPIE vol. 11047 (2019).

Hazra et al., Betatron resonance electron acceleration and generation of quasi-monoenergetic electron beams using 200fs Ti:Sapphire laser pulses, arxiv.org, Cornell University Library, 201 OLIN Library Cornell University Ithaca, NY 14853, Jun. 24, 2017, DOI: 10.1088/1361-6587/AAC97C.

Kneip et al., A plasma wiggler beamline for 100 TW to 10 PW lasers, High Energy Density Physics 8 (2012) 133-140.

Hur et al., Enhanced electron trapping by a static longitudinal magnetic field in laser wakefield acceleration, ScienceDirect, Physics Letters A 372 (2008) 2684-2687.

Vieira et al., Magnetic control of particle-injection in plasma based accelerators, Library Cornell University Ithaca, NY 14853, Jul. 26, 2011.

T. Tajima and J, Dawson, Laser Electron Accelerator, Phys. Rev. Lett. 43, 267 (1979).

E. Esarey et al, Overview of Plasma-Based Accelerator Concepts, IEEE Transactions on plasma science, vol. 24, 252 (1996).

E. Esarey et al, Self-Focusing and Guiding of Short Laser Pulses in Ionizing Gases and Plasmas, IEEE Journal of Quantum Electronics, vol. 33, 1879 (1997).

E. Esarey et al, Physics of laser-driven plasma-based electron accelerators, Rev. Mod. Phys. 81, 1229 (2009).

G.S Sarkisov et al., Self-focusing, channel formation, and high-energy ion generation in interaction of an intense short laser pulse with a He jet, Physical Rev. E, 59, 7042 (1999).

C. Joshi, Laser-Driven Plasma Accelerators Operating in the Self-Guided, Blowout Regime, IEEE Transactions on plasma Science, vol. 45, 3134 (2017).

7. A. Rousse et al., Production of a keV X-Ray Beam from Synchrotron Radiation in Relativistic Laser-Plasma Interaction, Phys. Rev. Lett. 93, 135005 (2004).

S. Fourmaux, et al, Demonstration of the synchrotron-type spectrum of laser-produced Betatron radiation, New J. of Physics, 13, 033017 (2011).

S. Corde et al, Femtosecond x rays from laser-plasma accelerators, Rev. Mod. Phys. 85, 1 (2013) and references therein.

* cited by examiner

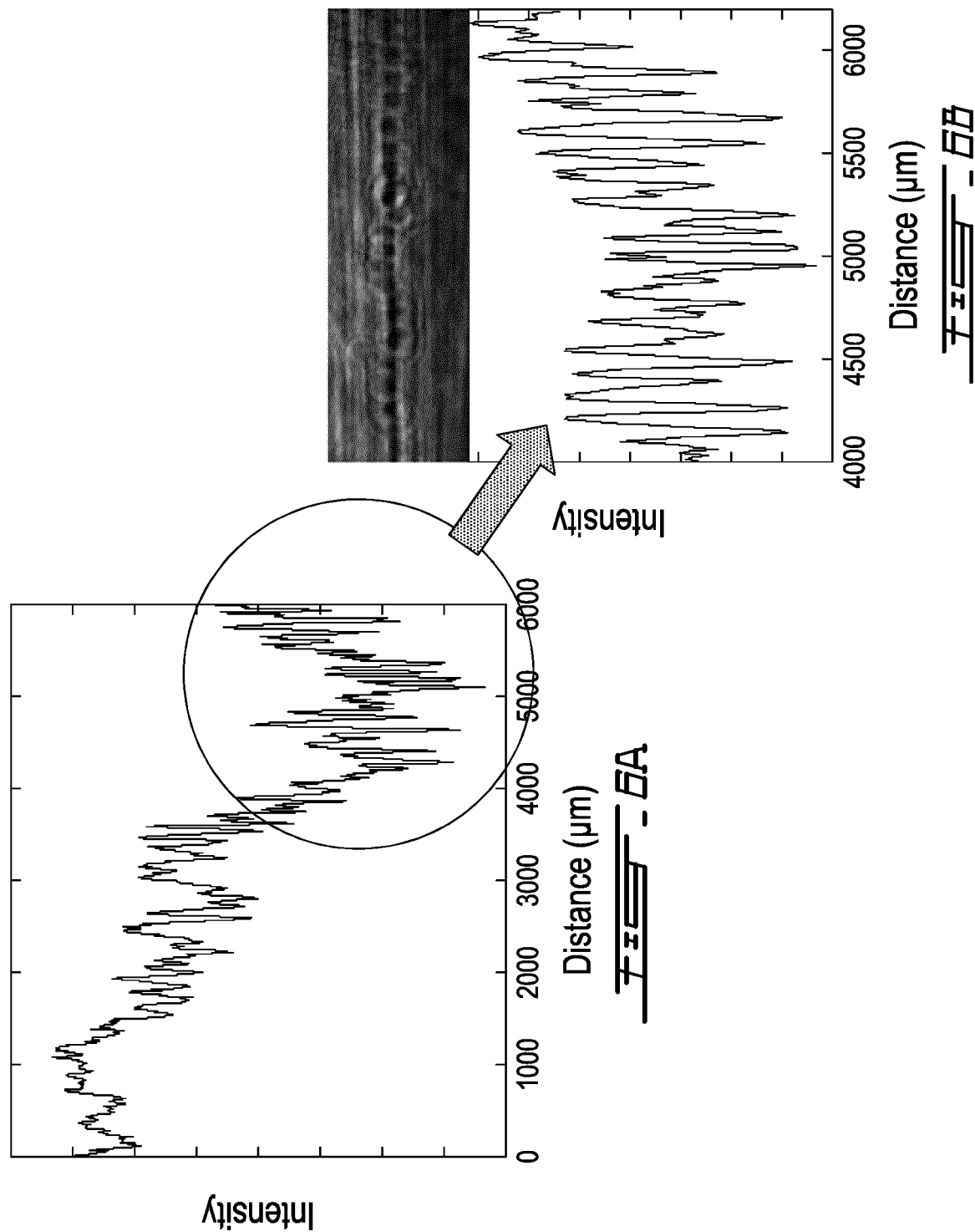

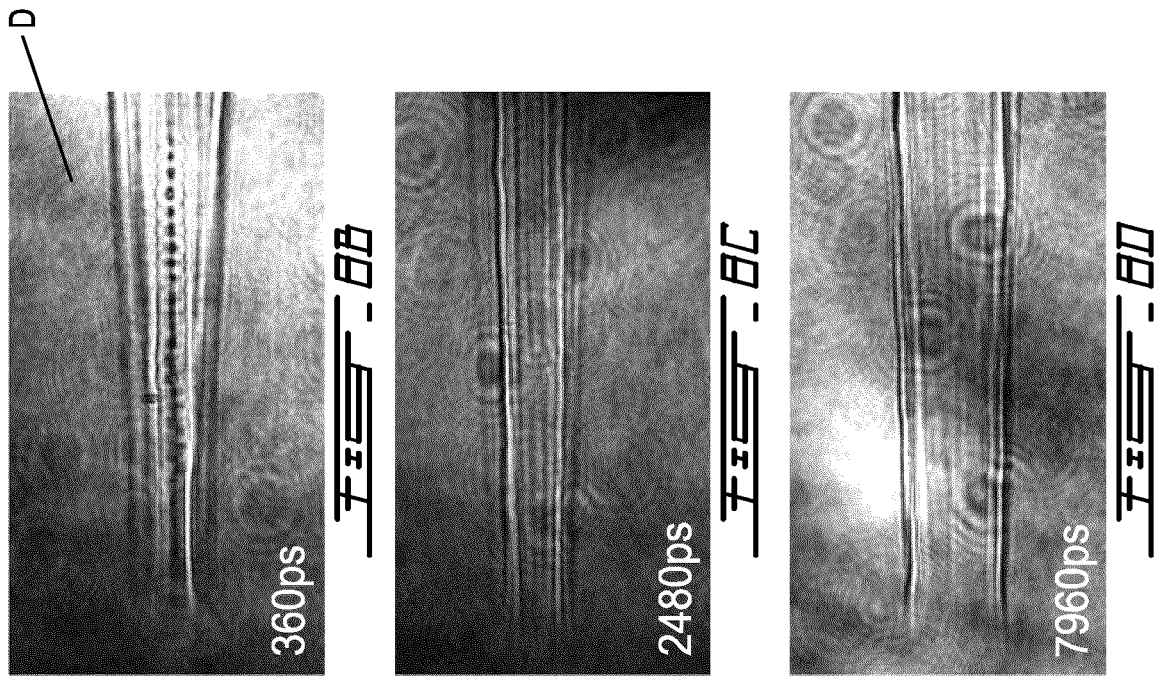
FIG. 8B
FIG. 8C
FIG. 8D
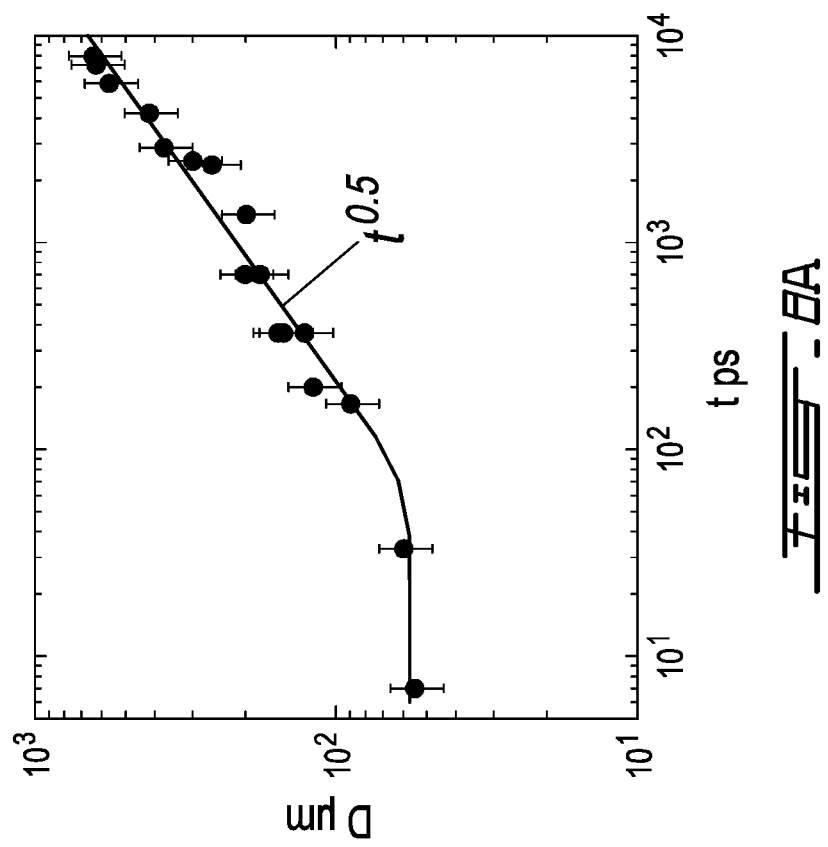
FIG. 8A

METHOD AND SYSTEM OF LASER-DRIVEN INTENSE X-RAY PHOTONS IMAGING

CROSS-REFERENCE TO RELATED APPLICATIONS

This application is a National Entry Application of PCT application no PCT/CA2019/050924 filed on Jul. 4, 2019 and published in English under PCT Article 21(2), which itself claims benefit of U.S. provisional applications Serial No's. 62/694,495 and 62/823,059, filed on Jul. 6, 2018 and Mar. 25, 2019 respectively. All documents above are incorporated herein in their entirety by reference.

FIELD OF THE INVENTION

The present invention relates to laser-driven X-ray photon sources. More specifically, the present invention is concerned with a method and a system of laser-driven intense X-ray photons imaging.

BACKGROUND OF THE INVENTION

In a plant production setting, a first issue is to see the interaction between plant's roots and the surrounding soil, which requires specific imaging technologies (X-rays or neutrons) with a high spatial resolution.

A second issue is to do a fast screening for selection. Plant breeders need to identify a phenotype in a production setting and determine if that phenotype is likely to be interesting to growers. A statistically significant number of samples, at least of order a thousand, typically need to be screened each growing cycle. Thus, for each plant line, no less than hundreds of screening samples per day must be achieved, which means about 10-12 minutes per plant.

High throughput phase contrast imaging for imaging of complex interfaces is being important in various fields, including plant science, and also material science and the biomedical field for example.

There is a need in the art for a method and system of laser-driven intense X-ray photons imaging.

SUMMARY OF THE INVENTION

More specifically, in accordance with the present invention, there is provided a X-ray source, comprising a laser, of a pulse duration of at most 40 fs, instantaneous power of at least about 80 TW, a pulse repetition rate of at least 1 Hz; an optical compressor spectrally shaping the laser beam; focusing optics in the range between f#10 and f#15; and a gas target of electron density after ionization by the laser beam in a range between $10^{18}$ cm$^{-3}$ and $10^{19}$ cm$^{-3}$; wherein the focusing optics focuses the laser beam in the gas target, and interaction of the focused laser beam with the gas target generates an X-ray beam, with a focused laser amplitude $a_0$, given by $a_0=0.855 \, [I_L \, (10^{18} \, \text{W/cm}^2) \, \lambda_L^2 \, (\mu m)]^{1/2}$, where $I_L$ is the on-target laser intensity and $\lambda_L$ is the laser wavelength, of at least 2 and a $P/P_c$ ratio value of at least 20, with P being the beam power and Pc a critical power given by $Pc=17 \, (n_c/n)$ GW where n is the electron density and $n_c$ is a critical electron density at which the plasma acts as a mirror reflecting the laser beam.

There is further provided a method for imaging an object, comprising placing the target at a distance from an X-ray source, and imaging with in-line geometry on a detector, wherein the X-ray source comprises a laser of a pulse duration of at most 40 fs, instantaneous power of at least about 80 TW, a pulse repetition rate of at least 1 Hz; an optical compressor spectrally shaping the laser beam; focusing optics in the range between f#10 and f#15; and a gas target of electron density after ionization by the laser beam in a range between $10^{18}$ cm$^{-3}$ and $10^{19}$ cm$^{-3}$; the focusing optics focusing the laser beam in the gas target, with a focused laser amplitude $a_0$, given by $a_0=0.855 \, [I_L \, (10^{18} \, \text{W/cm}^2) \, \lambda_L^2 \, (\mu m)]^{1/2}$, where $I_L$ is the on-target laser intensity and $\lambda_L$ is the laser wavelength, of at least 2 and a $P/P_c$ ratio value of at least 20, with P being the beam power and Pc a critical power given by $Pc=17 \, (n_c/n)$ GW where n is the electron density and $n_c$ is a critical electron density at which the plasma acts as a mirror reflecting the laser beam.

There is further provided a system for X-ray imaging, comprising a high power femtosecond laser, of a pulse duration of at most 40 fs, instantaneous power of at least about 80 TW and a pulse repetition rate of at least 1 Hz; an optical compressor spectrally shaping the laser beam; focusing optics in the range between f#10 and f#15; and a gas target of electron density after ionization by the laser beam in a range between $10^{18}$ cm$^{-3}$ and $10^{19}$ cm$^{-3}$; with a focused laser amplitude $a_0$, given by $a_0$, given by $a_0=0.855 \, [I_L \, (10^{18} \, \text{W/cm}^2) \, \lambda_L^2 \, (\mu m)]^{1/2}$, where $I_L$ is the on-target laser intensity and $\lambda_L$ is the laser wavelength, of at least 2 and a $P/P_c$ ratio value of at least 20, with P being the beam power and Pc a critical power given by $Pc=17 \, (n_c/n)$ GW where n is the electron density and $n_c$ is a critical electron density at which the plasma acts as a mirror reflecting the laser beam; and a target.

There is further provided a method for generating a plasma line, comprising propagating a laser beam from a laser, of a pulse duration of at most 40 fs, instantaneous power of at least about 80 TW and a pulse repetition rate of at least 1 Hz, with a focused laser amplitude $a_0$, given by $a_0$, given by $a_0=0.855 \, [I_L \, (10^{18} \, \text{W/cm}^2) \, \lambda_L^2 \, (\mu m)]^{1/2}$, where $I_L$ is the on-target laser intensity and $\lambda_L$ is the laser wavelength, of at least 2 and a $P/P_c$ ratio value of at least 20, with P being the beam power and Pc a critical power given by $Pc=17 \, (n_c/n)$ GW where n is the electron density and $n_c$ is a critical electron density at which the plasma acts as a mirror reflecting the laser beam, within a gas target of electron density after ionization by the laser beam in a range between $10^{18}$ cm$^{-3}$ and $10^{19}$ cm$^{-3}$; and applying a magnetic field.

There is further provided a method for guiding electromagnetic wave and electrical discharges, comprising propagating a laser beam from a laser, of a pulse duration of at most 40 fs, instantaneous power of at least about 80 TW and a pulse repetition rate of at least 1 Hz, with a focused laser amplitude $a_0$, given by $a_0$, given by $a_0=0.855 \, [I_L \, (10^{18} \, \text{W/cm}^2) \, \lambda_L^2 \, (\mu m)]^{1/2}$, where $I_L$ is the on-target laser intensity and $\lambda_L$ is the laser wavelength, of at least 2 and a $P/P_c$ ratio value of at least 20, with P being the beam power and Pc a critical power given by $Pc=17 \, (n_c/n)$ GW where n is the electron density and $n_c$ is a critical electron density at which the plasma acts as a mirror reflecting the laser beam, within a gas target of electron density after ionization by the laser beam in a range between $10^{18}$ cm$^{-3}$ and $10^{19}$ cm$^{-3}$.

There is further provided a method for object tomography, comprising imaging the object with X-ray beam generated by interaction of a laser beam with a gas target, wherein the laser beam is a spectrally shaped focused beam from a laser of a pulse duration of at most 40 fs, instantaneous power of at least about 80 TW and a pulse repetition rate of at least 1 Hz, with a focused laser amplitude $a_0$, given by $a_0$, given by $a_0=0.855 \, [I_L \, (10^{18} \, \text{W/cm}^2) \, \lambda_L^2 \, (\mu m)]^{1/2}$, where $I_L$ is the on-target laser intensity and $\lambda_L$ is the laser wavelength, of at least 2 and a $P/P_c$ ratio value of at least 20, with P being the beam power and Pc a critical power given by Pc=17 ($n_c$/n) GW where n is the electron density and $n_c$ is a critical electron density at which the plasma acts as a mirror reflecting the laser beam, and the gas target has an electron density after ionization by the laser beam in a range between $10^{18}$ cm$^{-3}$ and $10^{19}$ cm$^{-3}$.

There is further provided a method for generating a X-ray source, comprising selecting a laser of a pulse duration of at most 40 fs, instantaneous power of at least about 80 TW and pulse repetition rate of at least 1 Hz; spectrally shaping the laser beam; focusing the laser beam; and interacting the focused laser beam with a gas target of electron density after ionization by the laser beam in a range between $10^{18}$ cm$^{-3}$ and $10^{19}$ cm$^{-3}$, with a focused laser amplitude $a_0$, given by $a_0$, given by $a_0$=0.855 [$I_L$ ($10^{18}$ W/cm$^2$) $\lambda_L^2$ (µm)]$^{1/2}$, where $I_L$ is the on-target laser intensity and $\lambda_L$ is the laser wavelength, of at least 2 and a P/$P_c$ ratio value of at least 20, with P being the beam power and Pc a critical power given by Pc=17 ($n_c$/n) GW where n is the electron density and $n_c$ is a critical electron density at which the plasma acts as a mirror reflecting the laser beam.

There is further provided a high power laser system, comprising a beam shaper transforming an intensity distribution profile of the laser pulse into a Gaussian intensity distribution profile, wherein the beam shaper comprises at least one of: a graded reflective mirror, a graded transmission filter, a refractive transmission shaper, a spatial light modulator, and a deformable mirror to increase the laser pulse spatial contrast close to focus.

There is further provided a method for increasing a laser pulse spatial contrast close to focus, comprising shaping an intensity distribution profile of the laser pulse into a Gaussian intensity distribution profile.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 6A shows the intensity variation along the laser propagation axis on a shadowgraph measured at late time, i.e. 360 ps after the main laser, and showing focusing-defocusing effect through the entire gas length when a 20 fs pulse is incident with a 200 TW power ($a_0$ =5, P/$P_c$=40); FIG. 6B is a detail of FIG. 6A;

FIGS. 8 show the late expansion of the series of a micro plasma which develops in a cylindrical channel expanding like a blast wave: A) diameter as a function of time after the passage of the laser pulse; and transverse shadowgraphs B) after 360 ps; C) after 2480 ps; and D) after 7960 s;

DESCRIPTION OF ILLUSTRATIVE EMBODIMENTS

The present invention is illustrated in further details by the following non-limiting examples.

In a nutshell, there is presented a method and a system based on laser-based secondary sources of X-ray photons.

The Laser Wake-field Acceleration of electrons is based on the interaction of a short laser beam at relativistic intensity with a gas target, such as a gas or gas cell with cm length. A regime referred to as the bubble or blowout regime is reached for a laser amplitude $a_0$, given by $a_0$ =0.855[$I_L$ ($10^{18}$ W/cm$^2$) $\lambda_L^2$ (µm)]$^{1/2}$, where $I_L$ is the on-target laser intensity and $\lambda_L$ is the laser wavelength, of at least 2. In this regime ($a_0 \geq 2$), the electrons are accelerated over a length referred to as the dephasing length $L_d$, at large energies up to hundreds of MeV and more, and the laser energy is efficiently transferred to the electrons via the Laser Wake-field Acceleration (LWFA) process over a length referred to as the depletion length $L_p$. Channel formation through self-focusing may be used to accelerate particles. Self-focusing and filamentation are obtained with ultrafast laser pulses when the beam power P is above a critical power $P_c$ given by $P_c=17$ ($n_c/n$) GW where n is the electron density and $n_c$ is the critical density defining the electron density at which the plasma acts as a mirror reflecting the laser beam.

Figure 1:
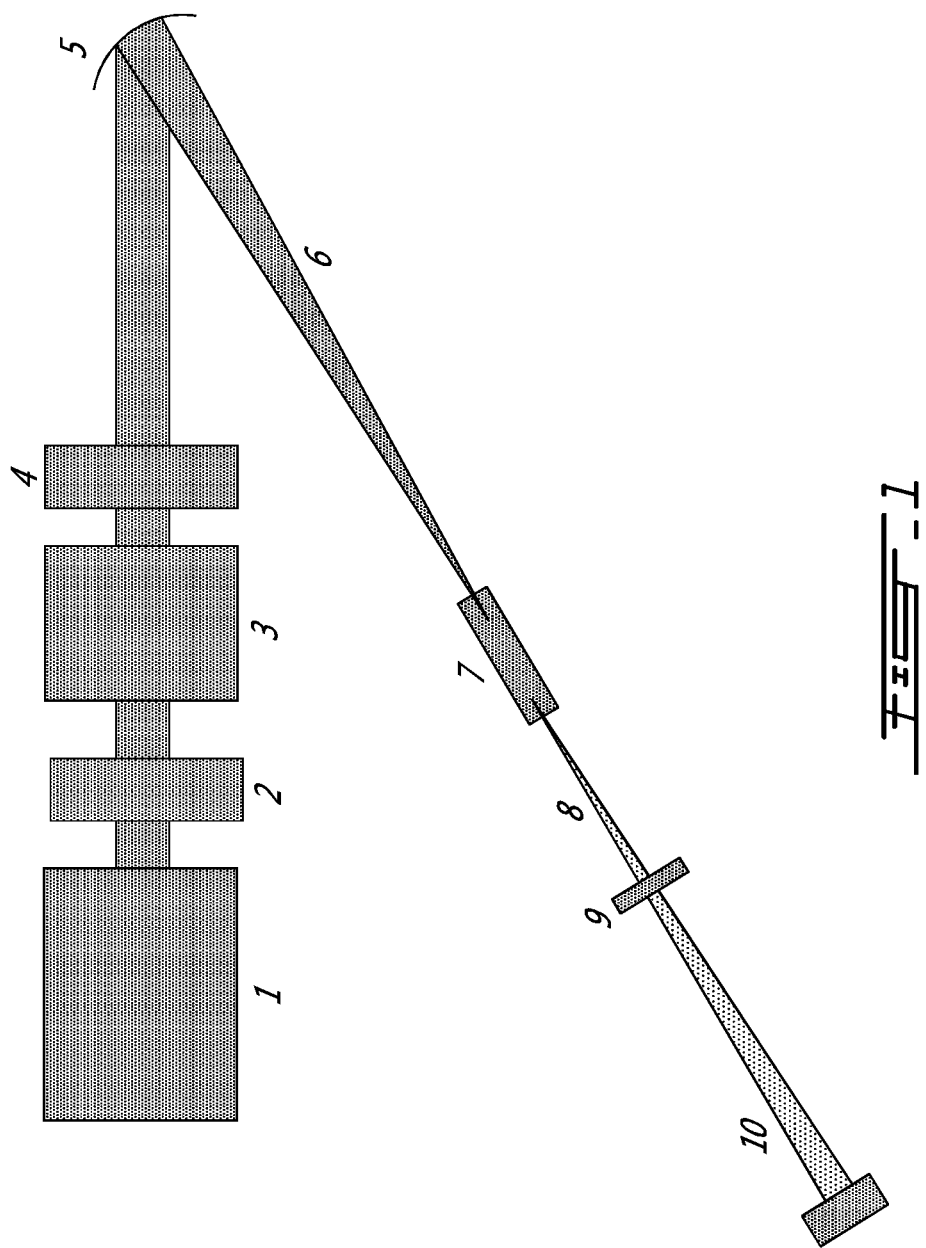
FIG. 1 is a schematic view of a system according to an embodiment of an aspect of the present invention.

A system as illustrated in FIG. 1 for example comprises a laser 1, a beam shaper 2, an optical compressor 3, focusing optics 5, a gas target 7 and an object 9 to be imaged with in-line geometry, and a detection system 10.

The laser 1 is selected to simultaneously optimize the laser amplitude ($a_0$), the Laser-Wakefield Acceleration (LWFA) interaction lengths and the relativistic focusing-defocusing process. In the present examples, the laser 1 is an 800 nm multi-terawatt laser system of instantaneous power of at least about 80 TW, for example in the range between about 80 TW and about 250 TW, with a laser energy on target in the range between about 2 J and about 5 J, a pulse duration of at most 40 fs, for example in the range between about 20 fs and about 34 fs, and a repetition rate of at least 1 Hz. The pulse duration is modified by shaping the width of the laser spectrum in a range between about 50 nm for the longer pulse, and about 90 nm for the shorter pulse. Other techniques for pulse compression may be used to produce even shorter pulse duration.

Figure 2:
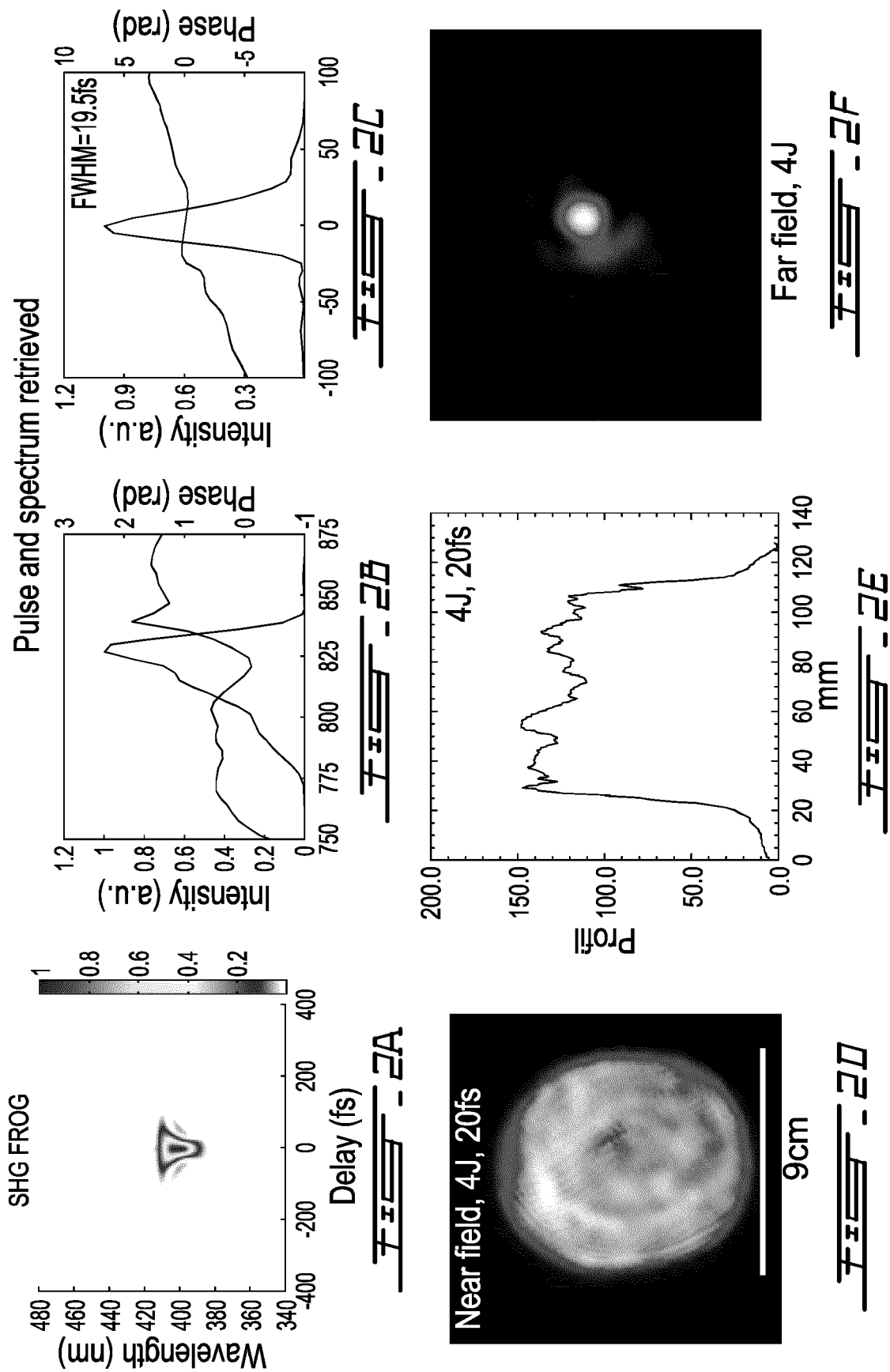
FIG. 2 show laser beam parameters used to generate the X-rays measured with a laser energy of 4 J and a 70 nm spectral bandwidth: A) the frog trace, indicating a pulse duration of 20 fs; B) pulse spectrum; C) pulse duration; D) the near field; E) the near field profile; and F) the far field.

Such laser system delivers a flat top beam profile. FIGS. 2 show an example of laser beam profiles in the near field (FIG. 2D) and the far field (FIG. 2F), and parameters measured at full energy with a laser energy of 4 J and a laser pulse of 20 fs. The far field distribution presents some low energy rings outside the main small spot (FIG. 2F).

Figure 3:
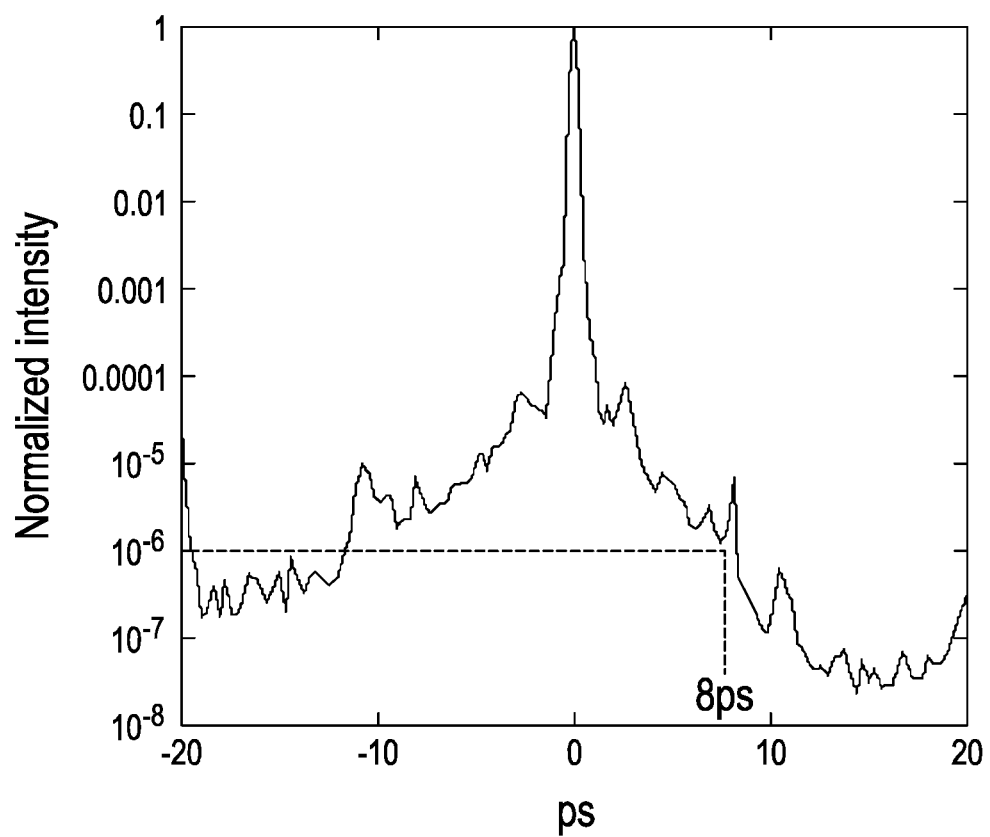
FIG. 3 shows laser pulse rise time of a laser system used to generate the X-rays as measured with a third order autocorrelator according to an embodiment of an aspect of the present invention.

Other profiles and parameters may be contemplated. FIG. 3 shows an example of a laser pulse rise time as measured with a third order autocorrelator. The contrast ratio is $10^{-6}$ at about 8 picoseconds before the peak of the pulse. A deformable mirror 4 at the output of the optical compressor 3 is used to monitor and control the laser beam phase front and the laser focusing.

The gas target 7 is typically a supersonic gas jet target.

The focusing optics 5 is selected in the range between f#10 and f#15, meaning between 10 and 15 times the beam diameter; in the present example an off-axis parabola of a 1.5 m focal length focal is used, providing a focused laser beam 6 with minimized aberrations in the gas target 7, the nozzle length being varied between 3 mm and 10 mm, in a spot diameter of about 15 μm for the central spot. The energy outside this most intense spot may contribute to produce a large volume of interaction. The on-target laser intensity $I_L$ on the gas target 7 is varied between $5\times10^{18}$ W/cm$^2$ and $5\times10^{19}$ W/cm$^2$. The field amplitude $a_0$ is varied between 1.5 and 5. The gas jet target electron density after ionization by the laser beam is adjusted between $10^{18}$ cm$^{-3}$ and $10^{19}$ cm$^{-3}$ in order to explore a range of the ratio $P/P_c$ between the beam power P and the critical power Pc between 4 and 80. The interaction of the focused laser beam 6 with the gas target 7 generates an X-ray beam 8. The object 9 placed at a distance from the gas target 7, acting as a X-ray source, is imaged with magnification with in-line geometry on the detector 10. The X-ray source optimization is realized by minimizing optical aberration to achieve laser propagation over the largest distance into the gas. Alignment and aberrations minimizing may be achieved as known in the art (see for example US patent application 2019/0165538), to control focusing of the laser beam and the generation of selected intensities on the gas target 7.

The measurements of electron spectra, X-ray angular profiles, X-ray spectra, X-ray yield and laser propagation inside the gas target were obtained simultaneously with various diagnostics for every single laser shot. An auxiliary beam with an appropriate delay line was used to realize transverse shadowgraphs of the plasma at different delays (ps–ns), with 15 μm resolution, as well as imaging through Thomson scattering of the plasma. Electron and X-ray diagnostics include measurements of electron spectrum (100 MeV–2 GeV), X-ray yield, X-ray spectrum (10 keV–100 keV), X-ray beam divergence, X-ray beam profile and shape stability, X-ray beam pointing stability.

During the laser pulse rise time, the intensity increases, with some radial distribution, above the ionization threshold and any small intensity or electron density fluctuation across the beam can start to increase through a convective filamentation instability. This instability non-linearly couples the spatial intensity and the density fluctuations and usually develops when the plasma length L is sufficiently large. For an intensity of $10^{13}$ W/cm$^2$ and 800 nm wavelength, the threshold length, given by $L/\lambda_L > 2\times10^2$ $(I_{14}\lambda^2_{\mu m})^{-1/3}$ where $I_{14}$ is the laser intensity normalized to $10^{14}$ W/cm$^2$, and $\lambda_L$ is the laser wavelength in μm, is about 500 μm, which is reached in the gas target and experimental conditions used in Laser-Wakefield Acceleration (LWFA) experiments.

The focusing of a flat top or a super-gaussian laser pulse results in a radial intensity distribution extending well outside the main focal spot and producing in the focal plane a ionized channel of a large diameter, typically of a few hundreds of μm. The filamentation instability may develop inside such channel, generating some profiling of the plasma density before the arrival of the main pulse. The convective instability optimized radial fluctuation wave number $k_x$, corresponding to a spatial wavelength $\lambda_x$, is given by $k_x^2/k_0^2 = 0.25$ $(v_{os}/v_{th})^2$ $(n/n_c)$, where $k_0$ is the laser wave number, $v_{os}$ is the quiver velocity of an electron in the laser field, and $v_{th}$ is the thermal velocity. For an intensity of $10^{13}$ W/cm$^2$, 800 nm wavelength, a density of $6\times10^{18}$ cm$^{-3}$ and a temperature of T=20 eV, the radial fluctuation has a typical spatial wavelength $\lambda_x$ of about 70 μm. The longitudinal spatial growth rate along the laser propagation axis is $K=(k_0/8)(v_0/v_{th})^2(n/n_c)$, where n is the electron density and $n_c$ is the critical density, and is about 0.5 mm$^{-1}$ for a 70 μm mode.

Figure 4:
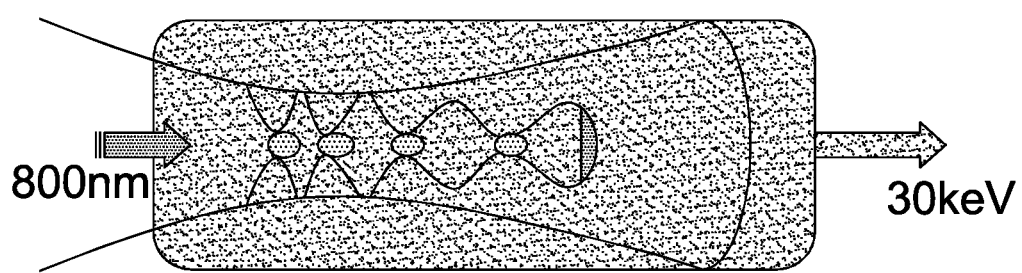
FIG. 4 is a schematic view of the propagation of the laser inside a gas target according to an embodiment of an aspect of the present invention.
Figure 5A:
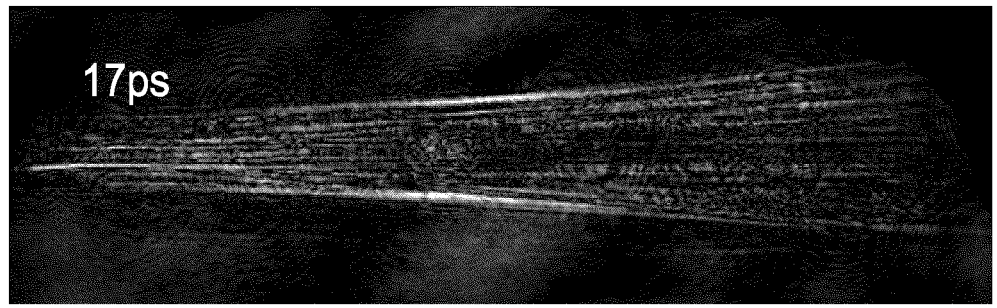
FIG. 5A shows a transverse shadowgraph measured at early time (17 ps) and FIG. 5B shows a transverse shadowgraph measured at late time (360 ps), after the passage of a 34 fs laser pulse (P=130 TW, 34 fs pulse duration, $a_0$ =3, P/$P_c$ =30, where P is the beam power and Pc is the critical power, focused at an intensity of $2 \times 10^{19}$ W/cm$^2$ at the entrance of the gas, $N_2$ gas, electron density of $6 \times 10^{18}$ cm$^{-3}$, 7 mm long nozzle)
Figure 5B:
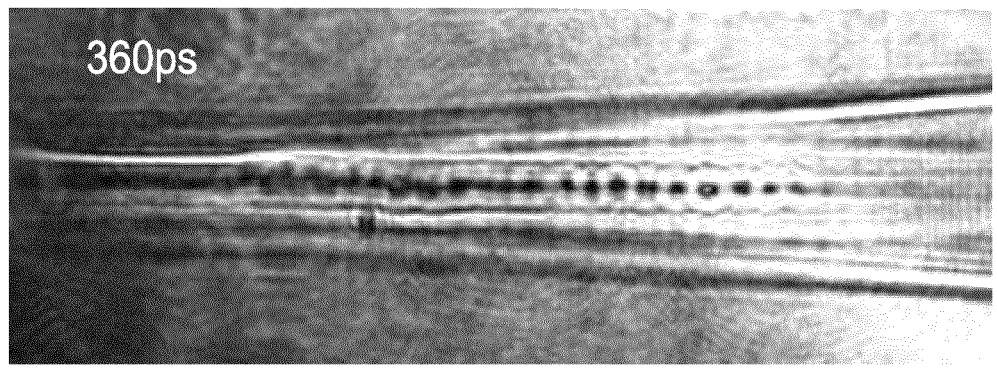

When the beam power P is well above the critical power $P_c$, the beam can undergo a number of focusing-defocusing cycles well beyond the theoretical Laser-Wakefield Acceleration (LWFA) dephasing and depletion lengths as shown schematically in FIG. 4. Transverse shadowgraphs measured at early time (17 ps) (FIG. 5A) and late time (360 ps) (FIG. 5B) after the passage of a 34 fs laser pulse (130 TW power, focused at an intensity of $2\times10^{19}$ W/cm$^2$ at the entrance of the gas target, $N_2$ gas, electron density of $6\times10^{18}$cm$^{-3}$ 7, mm long nozzle), show filamentation and self-focusing of the complex propagation of the laser pulse. In this example, the focusing-defocusing modulations extends over a length $L_{sf}$ which is about 4.2 mm, well beyond the dephasing and depletion lengths which are respectively around 1.3 and 2.6 mm in the present case. With a 20 fs pulse ($a_0$ =5) and higher $P/P_c$ ($P/P_c$~40) the self-guiding effect is generated over a length $L_{sf}$ of 7 mm (FIGS. 6), limited by the nozzle length.

Figure 7:
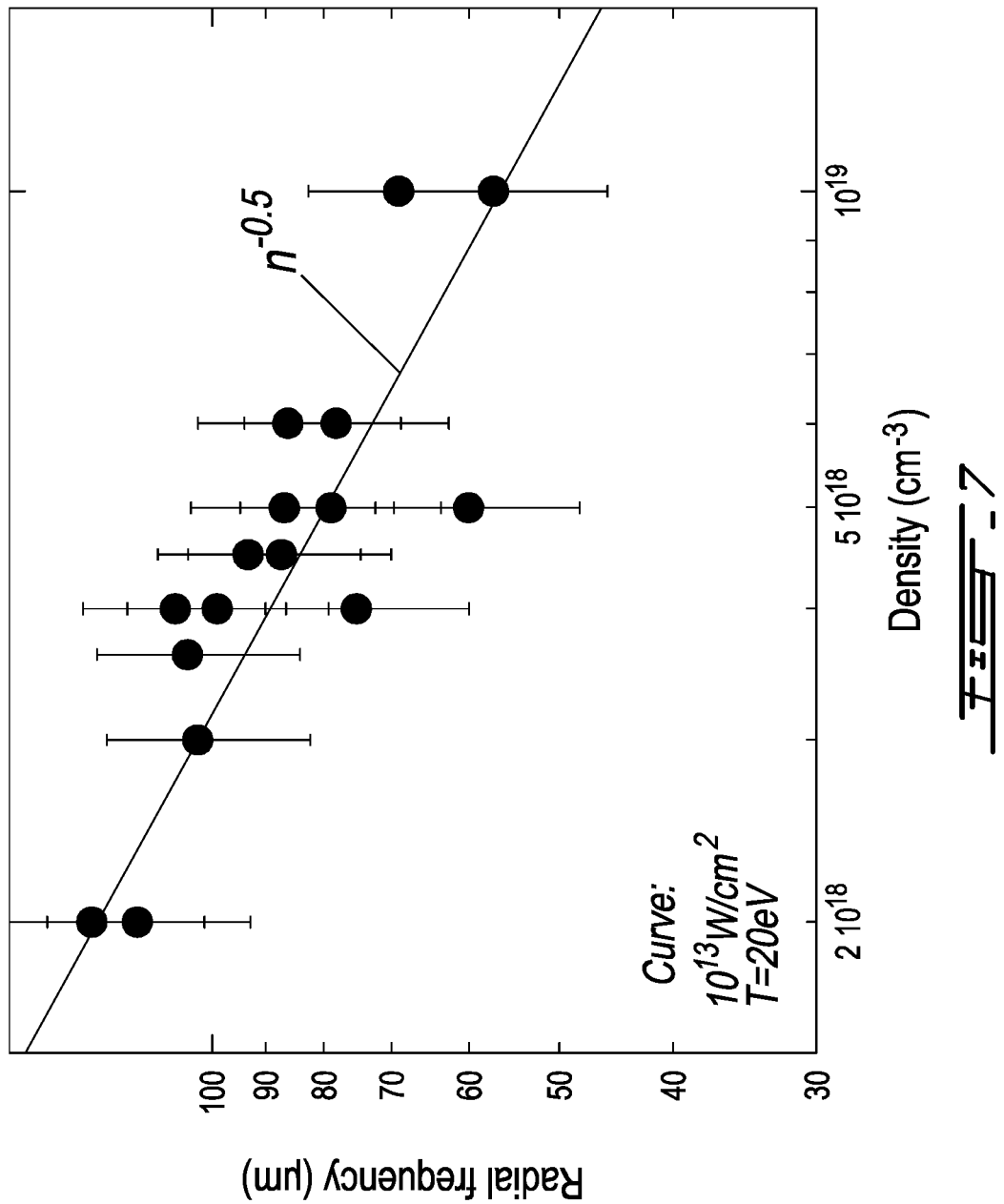
FIG. 7 shows the measured spatial wavelength of the radial fluctuation as a function of the gas electron density.

The radial distribution of the ionized region shows strong radial perturbations of the density whose imprint appears on the beam. The measured spatial wavelength of the radial fluctuation (with 20fs-25 fs pulse and peak intensity in the $4\times10^{19}$ W/cm$^2$–$4.5\times10^{19}$ W/cm$^2$ range) shown in FIG. 7 decreases from 120 μm to 60 μm when the electron density n increases from $10^{18}$cm$^{-3}$ to $10^{19}$ cm$^{-3}$ as n$^{-1/2}$, as expected from the scaling laws for the convective filamentation instability. The curve in FIG. 7 represents the calculated spatial wavelength for a laser intensity of $10^{13}$ W/cm$^2$, reached in the pulse rise time, and a temperature of 20 eV for the plasma produced by the radial intensity distribution.

The filamentation instability, by modulating the radial electron density profile of the gas target before the arrival of the main pulse during the rise time, may play an important role at higher peak power and laser intensities by assisting and increasing the self-guiding of the peak of the pulse. The large ionization channel and the filamentation effects are related to the intensity profile of a super-Gaussian distribution in the far field.

On longer time scales, each micro-plasma expands spherically. After some time, the micro-plasma expansions merge in a cylindrical channel expending radially as a Taylor-Sedov blast wave as shown in FIGS. 8.

In the system of FIG. 1, the beam shaper 2 is selected as a combination of optical elements including graded reflective mirror, graded transmission filter, refractive transmission shaper, spatial light modulator, deformable mirror, and/or spatial filtering, to transform the flat top or super-gaussian profile delivered by the laser into a Gaussian intensity distribution profile. A gaussian intensity distribution in the near field gives a similar gaussian distribution in the far field, which strongly reduces the radial extension of the ionization channel produced during the rise time of the laser and thus ensures that most of the laser energy is used efficiently to generate the self-guiding effect and bright X-rays. Before the compressor 3, at the output of the last amplification stage, it is thus used to mitigate the effect of the intensity spatial distribution in the far field and limit the energy spread outside the main focal spot in the far field.

Figure 9:
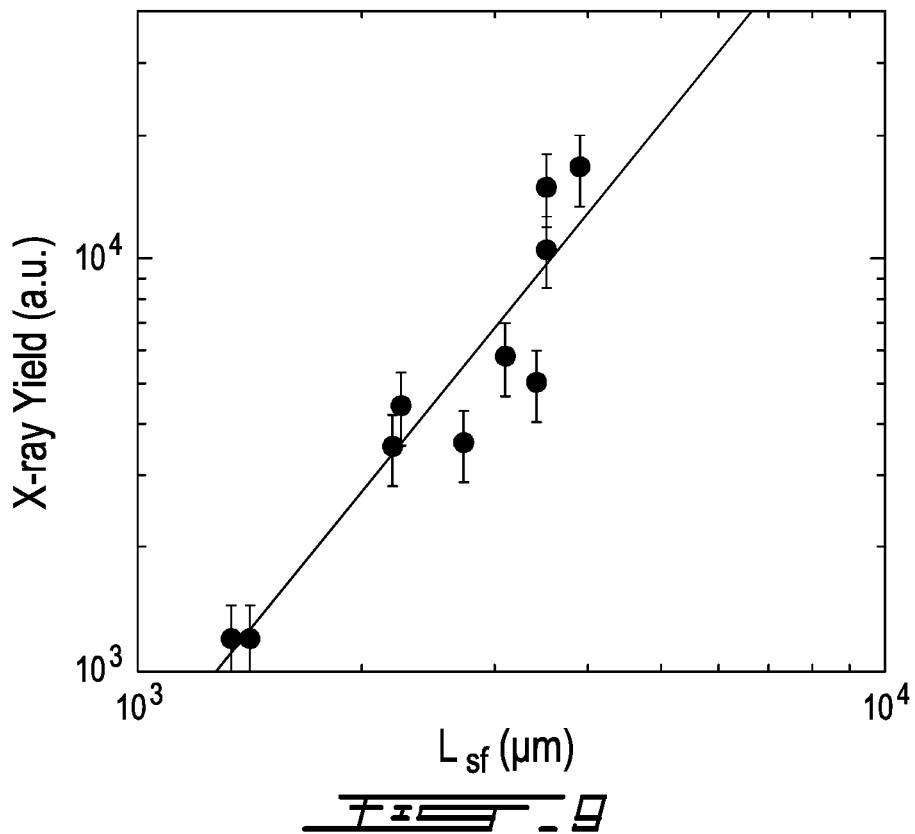
FIG. 9 shows the measured X-ray yield as a function of the self-guiding length.
Figure 10:
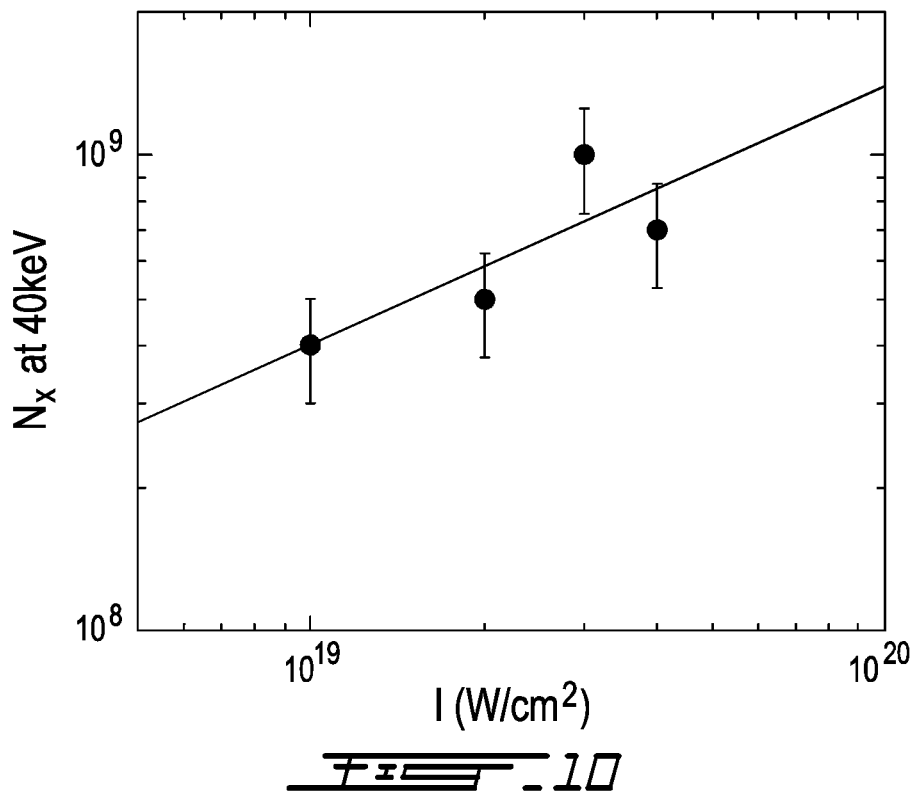
FIG. 10 shows the measured number of photons $N_x$ at 40 KeV, obtained from measured X-ray spectra, as a function of the laser intensity I; $N_x$ scales as $I^{1/2}$.
Figure 11:
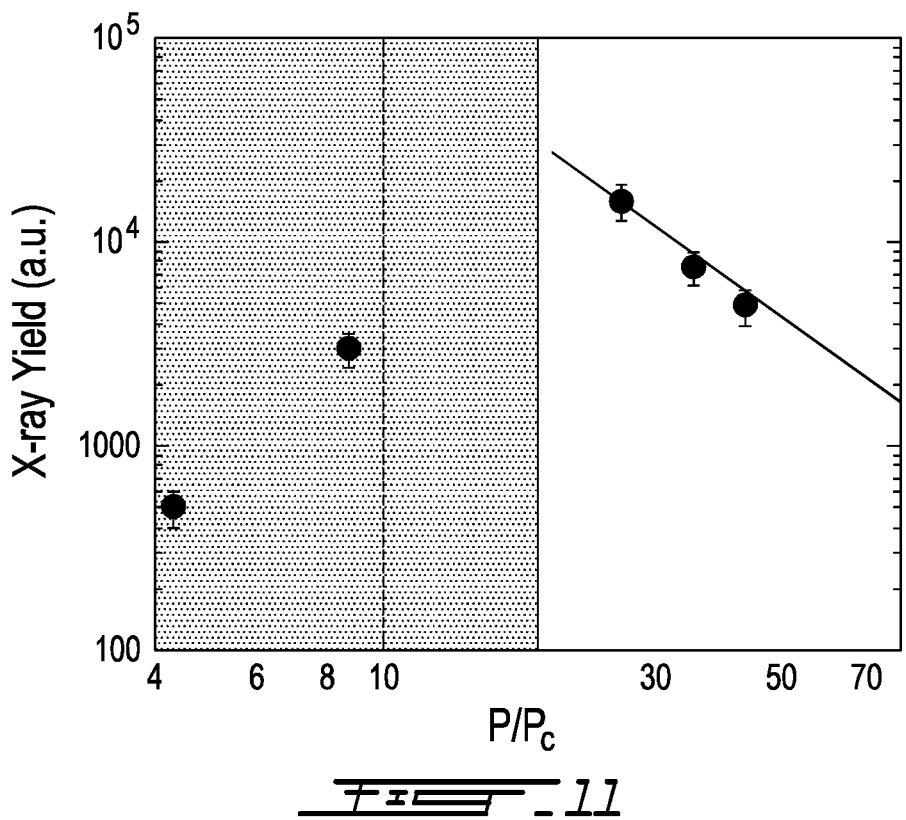
FIG. 11 shows the measured X-ray yield as a function of the gas target electron density; the X-ray yield scales as $1/(P/P_c)^2$ (or ($1/n_e^2$)) when P/$P_c$ is above 20.

The conjunction of very high P/P$_c$ ratio, with P/P$_c$ of at least over 20, and very short laser pulse, with pulse of at most 40 fs, for example about 20 fs, allows to reach a self-guiding regime. The X-ray yield (Y) scales as Y~$L_{sf}^2$ as shown in FIG. 9. The X-ray spectra, recorded in the self-guiding regime, indicate that the number of photons $N_x$ (in ph/(sr 0.1%BW shot) at 40 keV scales as $N_x \sim I_L^{1/2}$ ($N_x$=0.13 $I_L^{1/2}$ W/cm$^2$) (FIG. 10). In addition, FIG. 11 shows that below a density value corresponding to a P/P$_c$ ratio value of 20, the X-ray emission drops quickly when the density n and the ratio P/P$_c$ are decreased, and no Betatron signal is observed at $10^{18}$ cm$^{-3}$ (P/P$_c$=4.3) indicating a weak self-guiding effect in the lower density regime. For P/P$_c \geq 20$ the X-ray yield scales as Y~1/(P/P$_c$)$^2$ (or Y~1/n$^2$) as shown in FIG. 11.

These results allow to extract, in the high P/P$_c$ regime, where P/P$_c$ is 20 or higher, a scaling law correlating the focusing-defocusing length $L_{sf}$ and the photon number to the laser and gas target parameters. It can be deduced that $L_{sf} \sim a_0^{1/2} P_c$ which translates in (valid here for 40 keV photons and P/P$_c \geq 20$) $N_x \sim \alpha(P) a_0/n^2$ or $N_x = 10^{10} a_0^5$ (P/P$_c$)$^{-2}$ where $N_x$ is the number of photons at 40 keV in ph/(sr 0.1%BW shot), P the laser power, $a_0$ the field amplitude, and n the gas target density.

Figure 12:
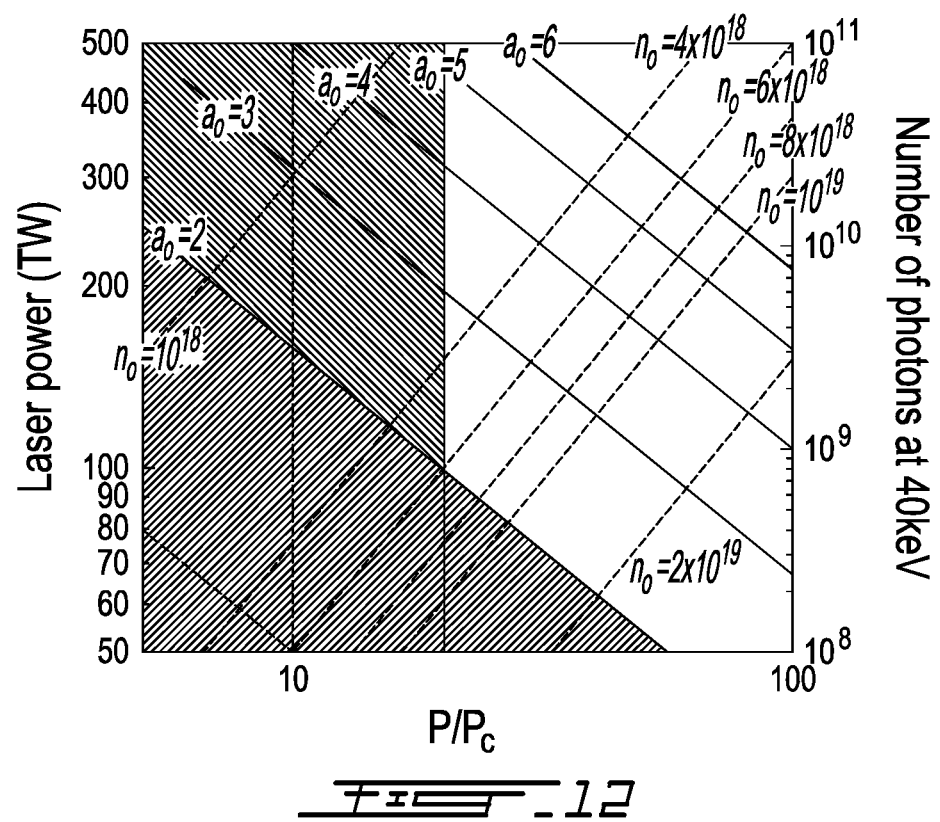
FIG. 12 is a design chart deduced from an empirical scaling law and relating the laser power P (TW), the ratio P/$P_c$ and the number of photons emitted at 40 keV (ph/sr 0.1%BDW shot); the zone outside the shade areas defining a regime of interest ($a_0 \geq 2$ and P/$P_c \geq 20$ )

A design chart shown in FIG. 12 has been established for this self-guiding regime ($a_0 \geq 2$ and P/P$_c \geq 20$) of X-ray production from the scaling law, correlating the number of photons $N_x$ at 40 keV, for the present example, to the laser power P and the field amplitude $a_0$, and to the gas target parameter (P$_c$). Starting from a laser power value (left vertical axis), the chart allows deducing the P/P$_c$ ratio for a given density (dotted line). Then, the interaction of the P/P$_c$ vertical line with a curve for a given $a_0$ indicates the number of photons expected for these parameters.

As an example, in the high P/P$_c$ regime, the following parameters were measured for the X-ray source (200 TW power, 2.5 Hz repetition rate, $4 \times 10^{19}$ W/cm$^2$, P/P$_c$ around 40, N$_2$ gas, 7 mm long nozzle): the critical energy, the slope of the synchrotron X-ray distribution spectrum, is in the range $E_c$=15 keV to 25 keV; the energy in the X-rays is 4 µJ/shot in the 30 keV-40 keV band, the X-ray source diameter is 1.5 µm (FWHM), the divergence of the X-ray beam is 50 mrad×50 mrad, the X-ray source repetition rate is 2.5 Hz, equal to the laser repetition rate. The beam spatial profile distribution, yield and pointing stabilities are around a few percent rms. The X-ray average power obtained is 10 µW(in the 30-40 keV band) and the photon number $N_x$ (at 40 keV)=10$^9$ ph/(sr 0.1%BW shot). The average power at 40 keV (2.5 Hz) is $8 \times 10^8$ ph/(s mm$^2$ mrad$^2$ 0.1%BW) and the brilliance at 40 keV is $1.6 \times 10^{22}$ ph/(s mm$^2$ mrad$^2$ 0.1%BW), assuming 20 fs X-ray pulse.

Similar design chart can be generated for different X-ray energies. A high throughput X-ray system for phase contrast imaging can thus be fully designed with the help of the design chart presented in FIG. 12.

Writing the scaling for the photon number as a function of the ratio P/P$_c$ gives, for constant focusing parameters, $N_x \sim a_0^5 (P/P_c)^{-2}$. Scaling of the X-ray photon number $N_x$, and of the energy $E_x$, in the X-ray beam in the 30 keV-40 keV band for example, as a function of the laser power, may be obtained by considering a trajectory for which P/(P$_c$)$^2$ is constant. Assuming constant focusing parameters and laser wavelength yields $E_x \sim \alpha^{5/2}(P/P_c)^3$ where $\alpha = P/(P_c)^2$.

Figure 13:
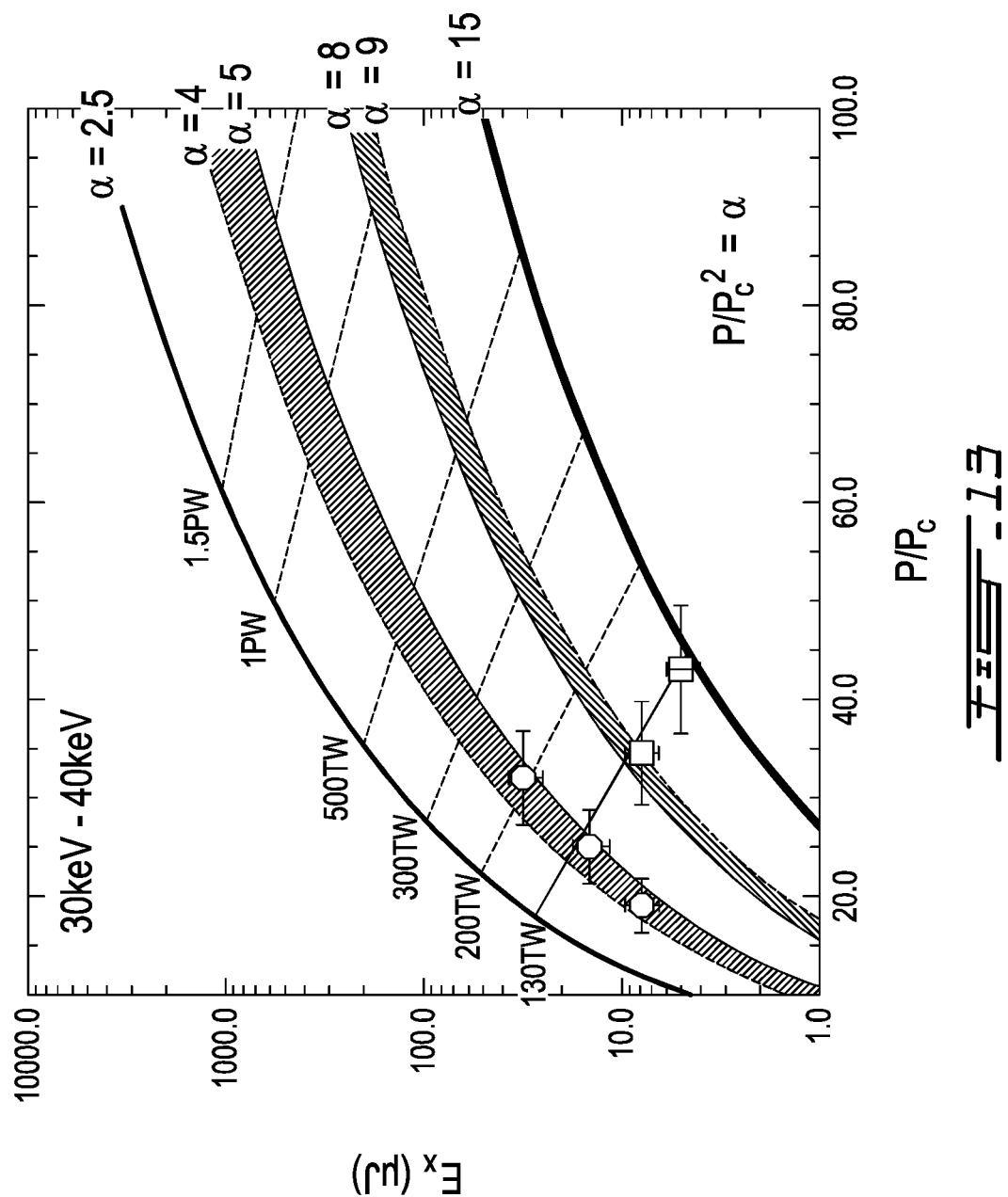
FIG. 13 shows the scaling of the energy $E_x$ in the X-ray energy band from 30 keV to 40 keV as a function of P/$P_c$ for various values of the parameter (P and $P_c$ being expressed in TW) and for various laser powers.

FIG. 13 shows of the energy $E_x$ as a function of P/P$_c$ for different values of the a parameter, P and P$_c$ being expressed in TW, and for different laser powers. The points represent data from experiments realized at different laser powers (90 TW, 120 TW and 220 TW) and with different a parameters (different powers for a between 4 and 5) and different α at constant power at 130 TW. In these experiments, all the parameters (P, gas density, laser intensity I and $E_x$ in the 30 keV-40 keV band) were experimentally measured, and each data point represents an average of several shots with the same conditions.

The method and system were used to demonstrate phase contrast high throughput imaging of plants with an in-line geometry. The distance between the X-ray source 7 and the object 9 and the distance between the object 9 and the detector 10, combined with the parameters of the detector 10 determine the imaging regime, the spatial resolution, and the field of view. These last parameters determine the number of acquisitions shots for a specific object to be imaged. In the present examples, the distance between the X-ray source 7 and the object 9 was in a range between about 70 and 90 cm and the distance between the object 9 and the detector 10 was in a range between about 70 and 300 cm; a first detector used was a direct detection CDD 1300×1340 pixels (pixel of a side length of 20 µm), and a second detector used was an indirect detection 2084×2084 pixels detector (pixel of a side length of 24 µm).

Figure 14B:
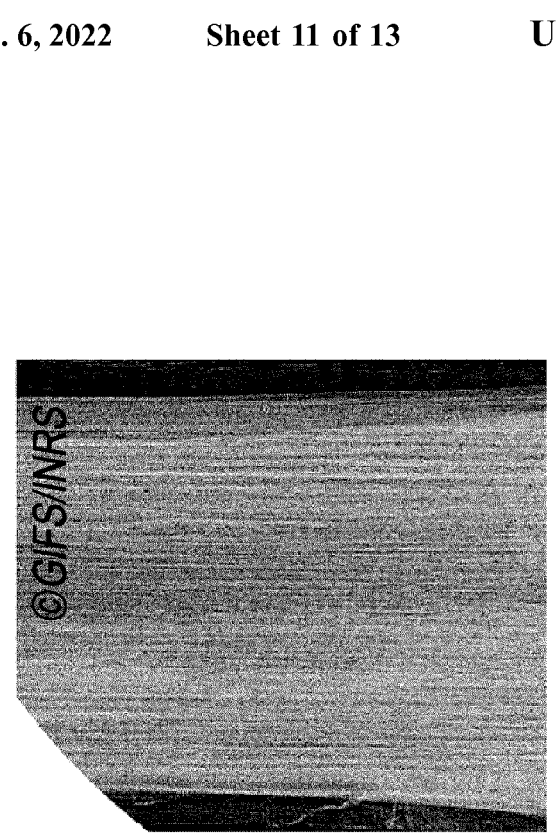
FIG. 14B shows a phase contrast image of poplar obtained in one laser shot.
Figure 14A:
FIG. 14A shows a phase contrast image of a wheat head obtained in one laser shot.
Figure 15A:
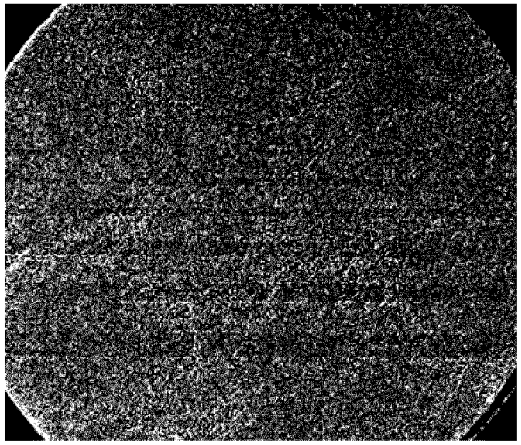
FIG. 15A is an image of a thick layer of soil.
Figure 15B:
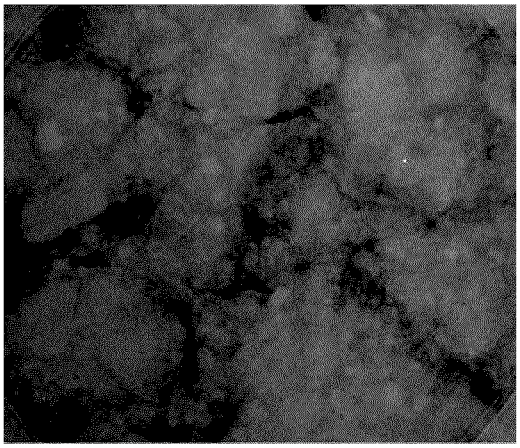
FIG. 15B is an image of a thick layer of soil with nylon fibers embedded therein.
Figure 15C:
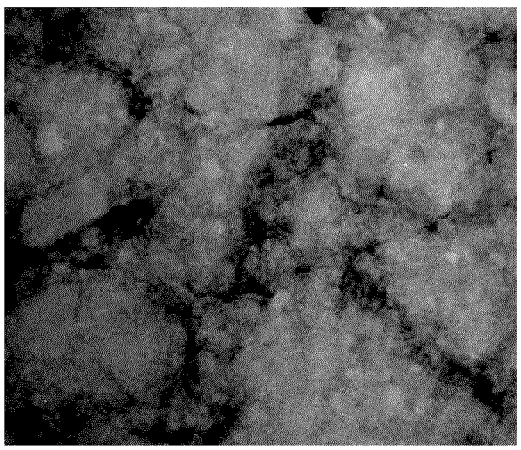
FIG. 15C is an image of the fibers embedded in the thick layer of soil retrieved with phase contrast information.
Figure 15D:
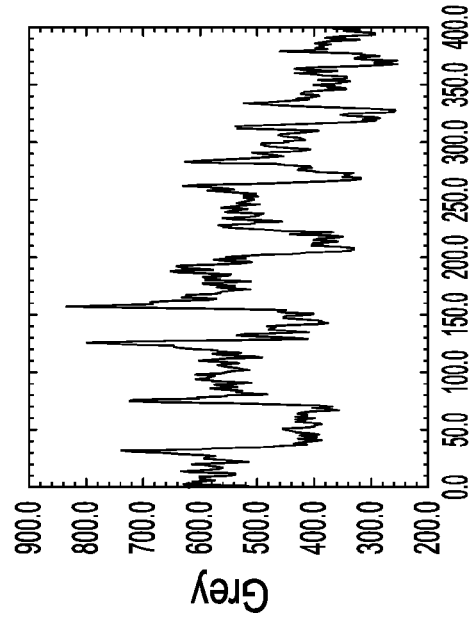
FIG. 15D shows a line out of an image of the fibers in air.
Figure 15E:
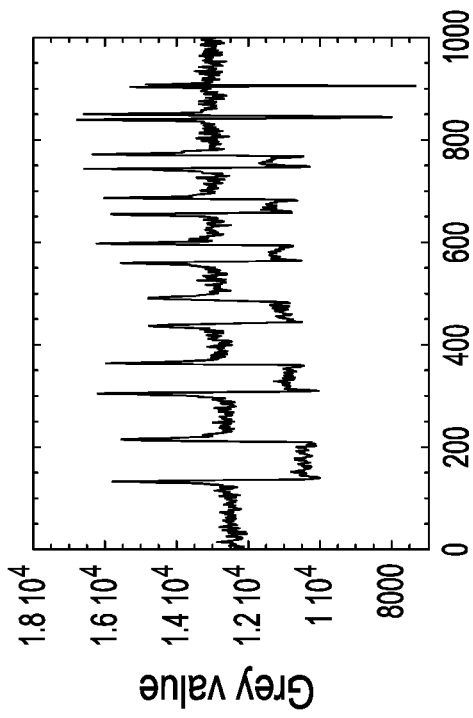
FIG. 15E shows a line out of the fibers (image (c)) in the soil.

Phase contrast images of a wheat head and a poplar obtained in one laser shot with a magnification of 3 are shown in FIG. 14A and FIG. 14B respectively. Comparison with images of same objects obtained with other techniques such as synchrotron or X-ray tubes for instance, indicates that the present method and system capture key features of a plant on a much faster data acquisition time. FIGS. 15 demonstrate that the X-ray imaging system allows visualization of transparent objects, such as nylon fibers with diameters ranging between 10 µm and 300 µm as illustrated, embedded inside an absorbing inhomogeneous and anisotropic environment, such as cm thick soil as illustrated. FIG. 15A presents the image (one laser shot) of a thick layer of soil without the fibers; FIG. 15B shows the image (one laser shot) of nylon fibers embedded in the thick layer of soil; FIG. 15C shows the image of the fibers embedded in the thick layer of soil and retrieved with phase contrast information; the line out of an image of the fibers in air and of the same fibers in the soil are shown in respectively FIGS. 15D and 15E. Phase contrast information is still visible in FIG. 15E, which indicates the potential of the method and the system.

3D tomography of plants with phase contrast have been realized on a time scale responding to the plant breeders needs with the production of 720 images (1 image per ½ degree) in 5 mn.

Figure 16:
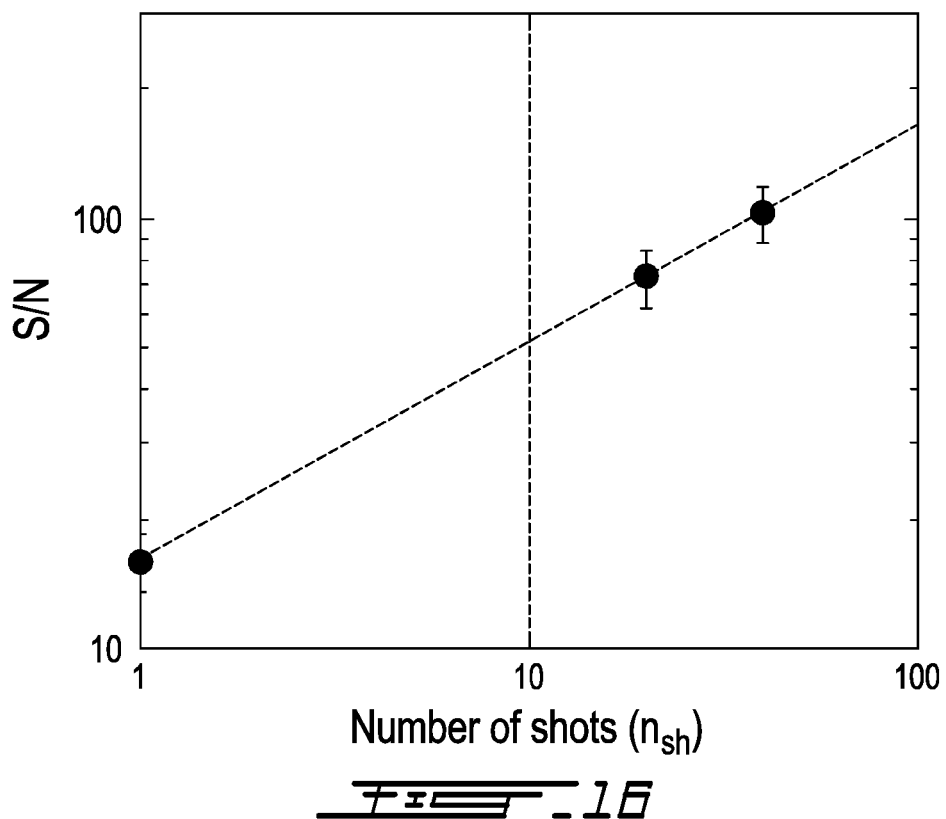
FIG. 16 shows the signal to noise ratio S/N as a function of the shot number obtained from images of nylon spheres (density 1.15) embedded in a 1.5 cm thick polyester resin (density 1.25) recorded with a magnification of 3.

The signal to noise ratio S/N, obtained with the X-ray source and deduced from images of nylon spheres (density 1.15) embedded in a 1.5 cm thick polyester resin (density 1.25) and recorded with a magnification of 3, is presented in FIG. 16 as a function of the shot number accumulated to obtain an image. A signal to noise ratio S/N of about 16 is obtained in one shot, and the scaling (S/N=16 $n_{sh}^{1/2}$) indicates that the signal to noise ratio S/N is proportional to the number of shots, demonstrating the good stability of the X-ray source.

The method can be used for in situ measurement of the laser intensity in a long focal length configuration, as used herein, from the knowledge of the gas target density ($P_c$) and from the measurement of $L_{sf}$. Indeed, the scaling law gives $I_L \lambda^2 = 21.8 [L_{sf}/P_c]^4$ where $I_L$ is in $10^{18}$ W/cm², $\lambda$ is in µm, $L_{sf}$ in mm and $P_c$ is in TW.

The combination of the present X-ray source emission high repetition rate, high number of photon per emission, homogeneity and stability of the X-ray beam, large field of view allowing to minimize the number of slices in which to image the object, hard X-ray energy ranges depending of the target parameters, for example 10 keV range for plant aerial parts, and 30-40 keV range for plant root system in the case of a plant, yields a method for fast screening and tomography of an object with a high spatial resolution.

Figure 17:
FIG. 17 is a phase contrast image of a mouse obtained in one laser shot and a magnification of 3.

The method was used for small animal single shot, high throughput phase contrast imaging and phase contrast 3D tomography as shown in FIG. 17.

The X-ray source as described herein may be used in conjunction with a magnetic field to obtain a compressed line plasma. As described hereinabove (see for example FIGS. 8), propagation of the laser beam within the gas jet target generates a series of micro-plasmas along the propagation axis of the laser; these micro-plasmas are compressed into a plasma line by application of a static or pulsed magnetic field.

Plasma canals provided by the generation of micro-plasmas along the propagation axis of the laser as a result of propagation of the laser beam within the gas jet target may further be used to generate low-density channels for guiding electromagnetic wave and/or electrical discharges.

There is provided a method and a system to improve the generation of laser-based secondary sources of photons or particles. The method and the system allow for spatial shaping of a laser beam used to generate intense beams of hard X-rays optimized for high throughput phase contrast imaging and rapid identification of phenotype in a plant production setting, for example. They allow an efficient use of all the laser energy, for example for the development of stand-alone system dedicated for plants and seeds high throughput X-ray phase contrast imaging.

The method and the system use laser pulses of at most 40 fs with a ratio of $P/P_c \geq 20$ to reach a self-guiding regime in which the laser drills a channel through the entire gas target length, well beyond the depletion and dephasing lengths, to produce very bright hard X-rays. The method and the system provide high throughput generation of LWFA-based betatron radiation in the hard x-ray range (10 keV-100 keV).

The method allows the generation of a long plasma channel over the entire gas target. The laser beam undergoes many focusing-defocusing cycles well beyond the theoretical Laser Wake-field Acceleration (LWFA) depletion length. In this regime obtained when the ratio $P/P_c$ is very large, the hard X-ray yield is proportional to the square of the self-guiding length which allows the production of high intensity hard X-ray beams appropriate for high throughput plant imaging. The Betatron X-ray source is characterized by a micrometric source size, a divergence of a few tens of mrad, a broad spectrum of synchrotron radiation with photon energies in the 10 keV-100 keV range, and a pulse duration similar to the femtosecond laser pulse duration.

A femtosecond high peak power laser system, delivering, at 800 nm wavelength, pulse with duration (FWHM) equal or less than 20 femtosecond with large energy larger than 3 J, and a target comprising a gas of typically 10 mm long were used. The quality of the laser beam controls the self-focusing and self-guiding length of the beam, which can then extend the X-ray production length well beyond the theoretical Laser Wake-field Acceleration (LWFA) depletion length. The laser pulse is focused at relativistic intensities (larger than $10^{18}$W/cm²) with a field amplitude $a_0 \geq 2$ to achieve the well-known Bubble regime. A key issue is to achieve a ratio $P/P_c \geq 20$ to reach this novel regime where the self-guiding effect and focusing-defocusing modulations are maintained over a length which is the total length of the gas target.

A unique regime of interaction is obtained, with focusing-defocusing self-guiding process maintained over the entire gas target length, by the conjunction of focusing the laser pulse inside the gas with a field amplitude $a_0$ larger than 2, using a very high $P/P_c$ ratio of at least 20 and a very short laser pulse of at most 40 fs, typically about 20 fs.

A scaling law is provided, correlating the focusing-defocusing length $L_{sf}$ and the photon number to the laser and gas target parameters. A design chart has been established for this regime of X-ray production from the scaling law, correlating the number of X-ray photons at a given energy to the laser power P and the field amplitude $a_0$, and to the gas target parameter (Ps).

The present invention provides the generation of high intensity beam of hard X-rays optimized for high throughput plant phase contrast imaging and allowing a rapid identification of phenotype in a plant production setting. The system and method have been used to realize phase contrast high throughput imaging of plants with an in-line geometry and very fast 3D phase contrast tomography compatible with plant production setting.

A number of applications may be considered other than in the plant and seed domains, such as, for example, measuring in situ the laser intensity in a long focal length configuration; doing small animal single shot, high throughput imaging and phase contrast 3D tomography; shaping and compressing plasmas; producing plasma channels to guide discharges; and material nondestructive imaging.

The scope of the claims should not be limited by the embodiments set forth in the examples, but should be given the broadest interpretation consistent with the description as a whole.

The invention claimed is:

1. A X-ray source, comprising:
a laser, of a pulse duration of at most 40 fs, instantaneous power of at least about 80 TW, a pulse repetition rate of at least 1 Hz;
an optical compressor spectrally shaping the laser beam;
focusing optics in the range between f#10 and f#15; and
a gas target of electron density after ionization by the laser beam in a range between $10^{18}$ cm$^{-3}$ and $10^{19}$ cm$^{-3}$;
wherein said focusing optics focuses the laser beam in the gas target, and interaction of the focused laser beam with the gas target generates an X-ray beam, with a focused laser amplitude $a_0$, given by $a_0 = 0.855 \, [I_L \, (10^{18} \, \text{W/cm}^2) \, \lambda_L^2 (\mu m)]^{1/2}$, where $I_L$ is the on-target laser intensity and $\lambda_L$ is the laser wavelength, of at least 2 and P/P$_c$ ratio value of at least 20, with P being the beam power and Pc a critical power given by Pc=17 (nc/n) GW where n is the electron density and nc is a critical electron density at which the plasma acts as a mirror reflecting the laser beam.

2. The X-ray source of claim 1, wherein said focusing optics is an off-axis parabola.

3. The X-ray source of claim 1, wherein said gas target is one of a supersonic gas jet target and a gas cell target.

4. The X-ray source of claim 1, further comprising a beam shaper transforming an intensity distribution profile of the laser pulse into a Gaussian intensity distribution profile.

5. The X-ray source of claim 1, further comprising a beam shaper transforming an intensity distribution profile of the laser pulse into a Gaussian intensity distribution profile, wherein the beam shaper comprises at least one of: a graded reflective mirror, a graded transmission filter, a refractive transmission shaper, a spatial light modulator, and a deformable mirror.

6. The X-ray source of claim 1, further comprising a deformable mirror at the output of the optical compressor, said deformable mirror controlling the laser beam phase front and laser focusing.

7. A method for imaging an object, comprising placing the target at a distance from an X-ray source, and imaging with in-line geometry on a detector, wherein the X-ray source comprises a laser of a pulse duration of at most 40 fs, instantaneous power of at least about 80 TW, a pulse repetition rate of at least 1 Hz; an optical compressor spectrally shaping the laser beam; focusing optics in the range between f#10 and f#15; and a gas target of electron density after ionization by the laser beam in a range between $10^{18}$ cm$^{-3}$ and $10^{19}$ cm$^{-3}$; the focusing optics focusing the laser beam in the gas target, with a focused laser amplitude $a_0$, given by $a_0 = 0.855 \, [I_L \, (10^{18} \, \text{W/cm}^2) \, \lambda_L^2 \, (\mu m)]^{1/2}$, where $I_L$ is the on-target laser intensity and $\lambda_L$ is the laser wavelength, of at least 2 and a P/P$_c$ ratio value of at least 20, with P being the beam power and Pc a critical power given by Pc=17 (nc/n) GW where n is the electron density and nc is a critical electron density at which the plasma acts as a mirror reflecting the laser beam.

8. The method of claim 7, comprising transforming an intensity distribution profile of the laser pulse into a Gaussian intensity distribution profile.

9. The method of claim, comprising selecting at least one of: a distance between the X-ray source and the object; a distance between the object and the detector, and parameters of the detector.

10. A system for X-ray imaging, comprising:
a high power femtosecond laser, of a pulse duration of at most 40 fs, instantaneous power of at least about 80 TW and a pulse repetition rate of at least 1 Hz;
an optical compressor spectrally shaping the laser beam;
focusing optics in the range between f#10 and f#15; and
a gas target of electron density after ionization by the laser beam in a range between $10^{18}$ cm$^{-3}$ and $10^{19}$ cm$^{-3}$; with a focused laser amplitude $a_0$, given by $a_0 = 0.855 \, [I_L \, (10^{18} \, \text{W/cm}^2) \, \lambda_L^2 \, (\mu m)]^{1/2}$, where $I_L$ is the on-target laser intensity and $\lambda_L$ is the laser wavelength, of at least 2 and a P/P$_c$ ratio value of at least 20, with P being the beam power and Pc a critical power given by Pc=17 (n$_c$/n) GW where n is the electron density and n$_c$ is a critical electron density at which the plasma acts as a mirror reflecting the laser beam; and
a target.

11. The system of claim 10, further comprising a beam shaper transforming an intensity distribution profile of the laser pulse into a Gaussian intensity distribution profile.

12. The system of claim 10, further comprising a deformable mirror at the output of the optical compressor, said deformable mirror controlling the laser beam phase front and laser focusing.

13. A method for generating a X-ray source, comprising selecting a laser of a pulse duration of at most 40 fs, instantaneous power of at least about 80 TW and pulse repetition rate of at least 1 Hz; spectrally shaping the laser beam; focusing the laser beam; and interacting the focused laser beam with a gas target of electron density after ionization by the laser beam in a range between $10^{18}$ cm$^{-3}$ and $10^{19}$ cm$^{-3}$, with a focused laser amplitude $a_0$, given by $a_0 = 0.855 [I_L \, (10^{18} \, \text{W/cm}^2) \, \lambda_L^2 \, (\mu m)]^{1/2}$, where $I_L$ is the on-target laser intensity and $\lambda_L$ is the laser wavelength, of at least 2 and a P/P$_c$ ratio value of at least 20, with P being the beam power and Pc a critical power given by Pc=17 (nc/n) GW where n is the electron density and nc is a critical electron density at which the plasma acts as a mirror reflecting the laser beam.

14. The method of claim 13, further comprising shaping an intensity distribution profile of the laser pulse into a Gaussian intensity distribution profile.

15. The method of claim 13, further comprising shaping an intensity distribution profile of the laser pulse into a Gaussian intensity distribution profile; and determining a number of photons of the X-ray source as a function of the laser power and the gas target of electron density.

16. The method of claim 13, further comprising applying a magnetic field, thereby generating a plasma line.

17. The method of claim 13, further comprising propagating the laser beam within a gas jet, of electron density after ionization in a range between $10^{18}$ cm$^{-3}$ and $10^{19}$ cm$^{-3}$.

18. The method of claim 13, comprising imaging an object with generated X-ray beam, wherein the gas target has an electron density after ionization by the laser beam in a range between $10^{18}$ cm$^{-3}$ and $10^{19}$ cm$^{-3}$.

* * * * *